United States Patent

Lokum et al.

(10) Patent No.: US 6,803,483 B2
(45) Date of Patent: Oct. 12, 2004

(54) PROCESS FOR THE PURIFICATION OF MIXTURES OF TOLUENEDIISOCYANATE

(75) Inventors: Heinrich Lokum, Kerpen (DE); Ove Nommensen, Burscheid (DE); Hermann Dallmeyer, Odenthal (DE); Wilhelm Hagen, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/457,105

(22) Filed: Jun. 9, 2003

(65) Prior Publication Data

US 2003/0233013 A1 Dec. 18, 2003

(30) Foreign Application Priority Data

Jun. 14, 2002 (EP) .............................. 02013461

(51) Int. Cl.⁷ ............................................ C07C 263/00
(52) U.S. Cl. ...................... 560/347; 560/352; 560/359
(58) Field of Search ............................. 560/347, 352, 560/359

(56) References Cited

U.S. PATENT DOCUMENTS

| 4,076,577 A | * | 2/1978 | Hetzel et al. ............... 159/47.1 |
| 4,851,570 A | | 7/1989 | Zaby et al. ................. 560/347 |
| 5,449,818 A | | 9/1995 | Biskup et al. .............. 560/347 |

OTHER PUBLICATIONS

Polyurethane Handbook Oertel G. (editor), Polyurethane Handbook, Munich, Germany: Hanser Publishers, (month unavailable) 1985, pp. 62–73, "Isocyanates" Dr. K. Schauerte.

Industrielle Aromatenchemie Franck H.–G and Stadelhofer J., Aromatenchemie, Berlin, Germany, Springer Verlag, (month unavailable) 1987"Herstellung und Verwendung on Toluel–Derivaten", p. 253.

Chem. System's PERP Report for TDI/MDI (Chem. Systems, Process Evaluation Research Planning TDI/MDI 99/99S8. Tarrytown, NY, USA: Chem. Systems (month unavailable) 1999, pp. 27–32.

Industrial & Engineering Chemistry Research, 35, (month unavailable) 1996, pp. 1877–1885, Omar Annakou and Peter Mizsey, "Rigorous Comparative Study of Energy–Integrated Distillation Schemes".

* cited by examiner

*Primary Examiner*—Rita Desai
*Assistant Examiner*—Hector M. Reyes
(74) *Attorney, Agent, or Firm*—Joseph C. Gil; Lyndanne M. Whalen

(57) ABSTRACT

A process for the purification of toluenediisocyanate by fractionating a crude distillation feed containing toluenediisocyante, an organic solvent and less than 2% by weight of phosgene in a heat integrated system having an upstream distillation column, an interchanger and a downstream distillation column which are connected in series. The vapor which is recovered from the upstream distillation column is used to reboil the bottoms product of the downstream distillation column or the feed to the downstream distillation column in the interchanger. The crude distillation feed comprising less than 2% by weight of phosgene is fractionated into three product fractions P1–P3 and optionally a fourth fraction P4. P1 is a noncondensible gas stream enriched with phosgene and/or low-boilers. P2 is a solvent-enriched product. P3 is a high boiler enriched bottoms product comprising toluenediisocyanate, and P4 is a toluenediisocyanate enriched stream lean in highboilers and reaction residues.

6 Claims, 4 Drawing Sheets

PROCESS FOR THE PURIFICATION OF MIXTURES OF TOLUENEDIISOCYANATE

CROSS REFERENCE TO RELATED PATENT APPLICATION

The present application claims the right of priority under 35 U.S.C. §119 (a)–(d) of European Patent Application No. 02013461.5, filed Jun. 14, 2002.

FIELD OF THE INVENTION

The present invention relates to an improvement of a toluenediisocyanate (TDI) recovery and purification process which uses a heat integrated system comprising two distillation columns connected in series for the fractionation of a crude isocyanate stream. The heat integration enables energy efficient operation for various feed rates, compositions and product specifications. The process of the present invention benefits from the ability to achieve a lower total manufacturing cost.

BACKGROUND OF THE INVENTION

The present invention relates to a process wherein toluenediamine is reacted with phosgene in the presence of a solvent solution in the liquid phase or wherein toluenediamine is reacted with phosgene directly in the gas phase with a solvent used in the quench cooling of said reaction; excess phosgene is then partially or completely removed from the resulting reaction mixture and the dephosgenated crude distillation feed is fed to a fractionation process wherein four fractions are recovered 1. a phosgene-enriched low-boiler product, which is recovered and returned to the dephosgenation or excess phosgene recovery process,
2. a relatively pure solvent product (less than 100 ppm by weight TDI) which is then reused in the phosgenation or excess phosgene recovery process,
3. a high-boiler (polymeric isocyanate, hydrolyzable chloride compounds (HCC), and other non-volatiles) enriched bottoms product which is sent to a residue removal system for the further recovery of volatiles,
4. and optionally an isocyanate-enriched product stream The field of art to which this invention pertains is a process for the purification of toluenediisocyanate (TDI) mixtures. TDI mixtures are generally produced by reacting toluene with nitric acid to yield dinitrotoluene (DNT), hydrogenating the resultant dinitrotoluene (DNT) to yield toluenediamine (TDA) and reacting the toluenediamine (TDA) with phosgene to give toluenediisocyanate (TDI). Toluenediisocyanate (TDI) is a commercial available material particularly useful in the preparation of polyurethanes, polyurea and polyisocyanurate polymers, especially foamed polymers.

DE-A1-3736988 teaches that organic mono- or poly-isocyanates are continuously prepared by reacting the corresponding mono- or poly-amine dissolved in an inert organic solvent with phosgene also dissolved in an inert organic solvent at a temperature under 150° C. The amine and phosgene solutions are combined and allowed to pass through one or more reaction columns connected below to above in series and having at least 10 chambers in total separated from each other by perforated plates, the holes of which preferably have a maximum diameter of 20 mm.

EP-A1-570799 teaches that production of aromatic diisocyanates is effected by reaction of diamines and phosgene. The phosgene and diamine are at above the boiling temperature of the diamine and the reaction has an average contact time of 0.5–5 seconds. The mixture is continuously passed through a cylindrical reaction space at 200–600° C. to complete the reaction with avoidance of back mixing. The gas mixture is then cooled to condense the diisocyanates, with the temperature being maintained above the decomposition temperature of carbamic acid chlorides corresponding to the diamines used. Uncondensed diisocyanate is washed out of the gas mixture with an inert solvent, and the inert solvent is recovered by distillation.

The *Polyurethane Handbook* (Oertel, G. (Editor), Polyurethane Handbook, Munich, Germany: Hanser Publishers, 1985, pp 62–73) gives a description of a state of the art for the phosgenation and distillation process for the production of toluenediisocyanate. In the distillation process, the solvent is completely removed from the crude TDI mixture as the top product from a solvent column, with this solvent being returned to the phosgenation or to the excess phosgene recovery. The remaining crude isocyanate bottoms stream from the solvent column is sent to a pre-flasher where two products are achieved: a isocyanate rich overhead product and a residue-enriched bottoms stream which is fed to the residue removal. In the residue removal, the volatiles are then removed from this residue-enriched stream and condensed. The condensed volatiles from residue removal together with the condensed overhead stream from the pre-vaporization are then combined and fed to an isocyanate column. In the isocyanate column, the product isocyanate is recovered as a top stream while a high-boiler enriched bottoms stream is returned to the pre-vaporization step. This process is limited by the fact that the complete solvent removal is performed in one solvent column. While it is known that TDI yields are negatively affected by higher temperatures, complete solvent removal necessitates operating under relatively low pressures to achieve sump temperatures low enough to prevent a loss of yield, thus necessitating a large column. Moreover, the long residence time of isocyanate together with residue in heating zones can lead to a higher rate of residue formation. Finally, condensation of the overhead stream from the pre-vaporization before feeding to the isocyanate column is energy inefficient.

In *Industrielle Aromatenchemie* (Franck H.-G. and Stadelhofer J., Industrielle Aromatenchemie. Berlin, Germany: Springer Verlag, 1987, p 253) a second state-of-the-art process is described. In the described process, the crude TDI-solvent mixture is fed to a two-step pre-vaporization step resulting in a low-boiling overhead vapor product and solvent-free residue-enriched bottoms product which is fed to the residue removal. In the residue removal process, the volatiles are then removed from this residue-enriched stream and condensed. The overhead product from the pre-vaporization is fed to a solvent column. In the solvent column the solvent is completely removed as the top product, with the solvent being returned to the phosgenation or to the excess phosgene recovery. The remaining crude isocyanate bottoms stream from the solvent column is fed along with the condensed volatiles from residue removal to an isocyanate column. In the isocyanate column, the product isocyanate is recovered as a top stream while a high-boiler (polymeric isocyanate and hydrolyzable chloride compounds (HCC), and other non-volatiles) enriched bottoms stream is returned to the pre-vaporization step. This process is also limited by the fact that the complete solvent removal must be performed in one solvent column. As in the process described in the *Polyurethane Handbook*, complete solvent removal necessitates operating under relatively low pressures to achieve sump temperatures low enough to prevent a loss of yield, resulting in a large solvent column. However, this process, in comparison with the former process achieves a reduced residence time of isocyanate together with residue in heating zones possibly leading to a lower rate of residue formation. Moreover, because there is no needless condensation of a vapor feed to the isocyanate column, this process will be more energy efficient.

From Chem. System's *PERP Report for TDI/MDI* (Chem. Systems, Process Evaluation Research Planning TDI/MDI 98/99S8. Tarrytown, N.Y., USA: Chem. Systems, 1999, pp 27–32) for TDI/MDI it can be learned, that the fractionation of a crude TDI distillation feed product can be completed in the following manner. Normally, the liquid product from the dephosgenation stage is sent to a pre-vaporizer which produces a residue-rich liquid phase as a bottom product and a vapor-phase product containing mainly solvent and isocyanate as an overhead product. The bottom product from the pre-vaporization is sent to a process for the removal of volatile compounds from the reaction residues (residue removal). The volatile components removed in the residue removal stage as well as the vapor-phase product from the pre-vaporizer are sent to a solvent column, where an initial separation of the isocyanate from solvent is completed as well as the removal of any remaining phosgene. The resulting products are a phosgene-enriched top product, a relatively pure solvent stream as an intermediate product and an isocyanate-enriched bottoms product. The phosgene stream is then returned to the dephosgenation process or to the excess phosgene recovery process. The solvent product is then used in the phosgenation section as well as in the excess phosgene recovery. The bottoms isocyanate-rich product is then sent to a second solvent removal column where the remainder of the solvent is removed. The top solvent product from this step, when relatively pure, can be used in phosgenation or excess phosgene recovery or can be returned to the primary solvent removal step. The final solvent-free bottoms isocyanate product is sent to an isocyanate column, resulting in an isocyanate top product and a residue and hydrolyzable chloride compound (HCC) enriched-bottom stream which is returned to the pre-vaporization or to the residue-removal stages. This process, like the process described in *Industrielle Aromatenchemie*, in comparison with the process described in the *Polyurethane Handbook* achieves a reduced residence time of isocyanate together with residue in heating zones possibly leading to a lower rate of residue formation. Additionally, like the process described in *Industrielle Aromatenchemie*, because there is no needless condensation of a vapor feed to the isocyanate column, this process will be more energy efficient than the process disclosed in the Polyurethane Handbook. It holds the additional advantage that the solvent removal is completed in two steps. By taking advantage of the solvent having a lower boiling point than the isocyanate, the majority of the solvent can be removed under higher pressure, therefore, reducing the necessary investment cost for the solvent removal. Additionally, the use of two solvent removal steps adds to the flexibility of operation. However, the presence of a third column adds more complexity to the process.

In fractionation, it is sometimes desirable to separate a multi-component feed stream into a number of streams containing various fractions of desirable components in the product streams. For the case of one feed stream and two product streams, the separation can be accomplished by distillate and bottoms product draw. Further separation can be accomplished by repeating the two-product stream process to either the distillate or the bottoms streams. However, the introduction of additional columns will require a corresponding number of reboilers and condensers. That requirement, in turn, requires additional operating costs as the condensing and the reboiling process is being repeated. Numerous references can be found in prior art documenting efforts to lower both capital and operating costs in the separation of several fractions from a multi-component feed stream.

One potential way to decrease the energy process is the integration of energy between two columns in a fractionation system. (Annakou, O and Mizsey, P, *Rigorous Comparative Study of Energy-Integrated Distillation Schemes*, Industrial & Engineering Chemistry Research, 1996, 35, pp 1877–1885). In such a configuration, the vapors from one column are condensed to provide the energy to reboil the bottoms product of the other column. This can either be performed in a process wherein the vapor of the upstream distillation column is used to reboil the bottom product of the downstream distillation column or conversely, where the vapors of the downstream column are used to reboil the bottoms product of the upstream column.

Generally, the development of the process for TDI recovery has resulted in reductions in capital investment, greater energy efficiency, and improved product yield. But, the energy consumption, capital investment and product yield is still insufficient.

BRIEF SUMMARY OF THE INVENTION

In the present invention, the use of a system of heat integrated distillation columns wherein the heat of the vapor of the upstream distillation column is used to vaporize the feed to the downstream column or to reboil the bottom product of the downstream distillation column for the partial or total removal of solvent allows for a surprising reduction in the energy required to complete the TDI distillation process.

DETAILED DESCRIPTION OF THE INVENTION

Figure 1:
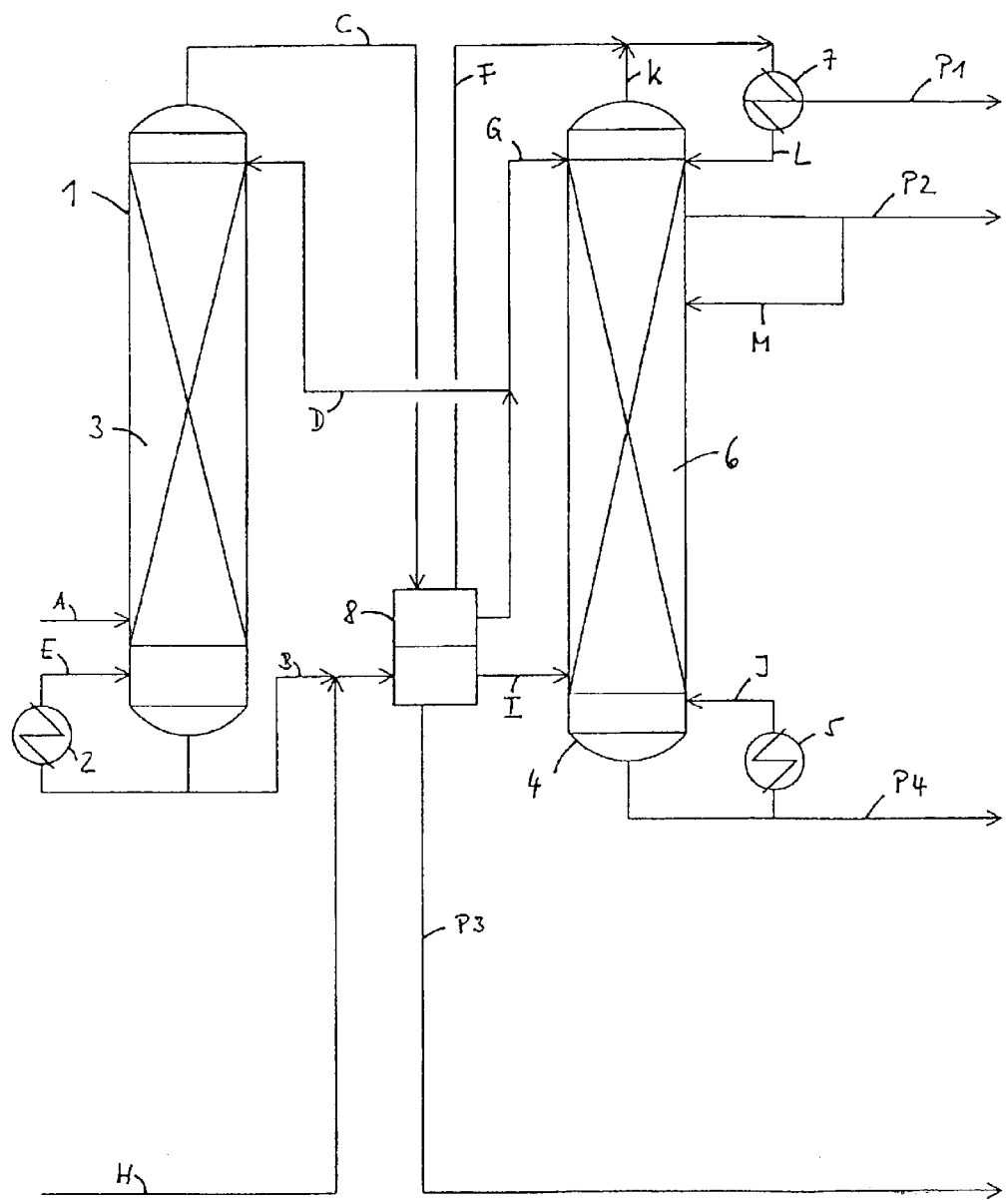
FIG. 1 is a schematic diagram of a first heat integrated system comprising an upstream distillation column and a downstream distillation column which are connected in series.

The invention is directed to a process for the purification of toluenediisocyanate by fractionating a crude distillation feed comprising toluenediisocyanate, an organic solvent and less than 2% by weight of phosgene in a heat integrated system comprising an upstream distillation column, an interchanger and a downstream distillation column which are connected in series, whereby the vapor which is recovered from the upstream distillation column is used to reboil the bottoms product of the downstream distillation column or the feed to the downstream distillation column in the interchanger,
and whereby the crude distillation feed comprising less than 2% by weight of phosgene is fractionated into three product fractions P1–P3 and optionally a fourth product fraction P4, whereby P1 is a noncondensible gas stream enriched with phosgene and/or low-boilers, P2 is a solvent-enriched product, P3 is a high boiler enriched bottoms product comprising toluenediisocyanat and P4 is a toluenediisocyanate enriched stream lean in high-boilers and reaction residues.

In the phosgenation according to the state of the art, toluene diamine is reacted with phosgene in the presence of a solvent solution in the liquid phase or with phosgene directly in the gas phase with a solvent used in the quench cooling of said reaction. The resulting reaction mixture preferably has a composition of 5–40% by weight toluenediisocyanate, 1–2% by weight hydrogen chloride, 1–5% by weight phosgene, 0.1–2% by weight high-boilers (polymeric isocyanates, hydrolyzable chloride compounds (HCC)), and the rest being solvent. Hydrolyzable chloride compounds are generally defined as compounds in which the available chlorine is "loosely" bound. Illustrative of these compounds are the following species: $ClCH_2C_6H_3(NCO)_2$ and $(CH_3NCOCl)CH_3C_6H_3(NCO)$.

The content of hydrolyzable chloride compounds is generally determined by reacting the available chorine in the sample with a hot water-alcohol solution resulting in HCl and a subsequent titration to determine the hydrolyzable chlorine concentration. This value is generally reported as weight fraction hydrolyzable chlorine" (HC).

Chlorinated aromatic hydrocarbons are species in which the chlorine is "tightly" bound. Illustrative of such compounds are the common solvents o-dichloro-benzene, and chlorobenzene, and related compounds.

After the reaction the resulting reaction mixture is fed to a separation step if the reaction mixture (crude distillation feed) comprises 2% by weight or more of phosgene. In this separation step, the excess phosgene is at least partly removed resulting in crude distillation feed comprising less than 2% by weight of phosgene. The separation of the phosgene can be performed using many different methods or combinations thereof. Examples of these methods are simple vapor/liquid flash separation, with or without the increase of temperature or a decrease in pressure, gas stripping, distillation, etc.

The resulting crude distillation feed comprising less than 2% by weight of phosgene is then fed to the heat integrated distillation system comprising an upstream distillation column and a downstream distillation column which are connected in series and fractionated into the three product fractions P1–P3, and optionally a product fraction P4.

Product Fraction P1 is a phosgene-enriched low-boiler product preferably comprising 20–50% by weight of phosgene and other low boilers such as chlorobenzene, tetrachloromethane, trichloromethane and dichloromethane, 20–49% by weight of solvent, the rest being noncondensable gases, i.e. air, hydrogen chloride, etc. The condensable species are preferably recovered and returned to the dephosgenation or excess phosgene recovery process.

Product Fraction P2 is a solvent enriched product which is then preferably reused in the phosgenation or excess phosgene recovery process. The fraction P2 preferably comprises solvent with an isocyanate concentration and a phosgene concentration of less than 100 ppm by weight, respectively.

Product Fraction P3 is a high-boiler and residue enriched bottoms product which is preferably sent to a residue removal system for the further recovery of volatiles. The fraction P3 preferably comprises 0.5–15% by weight high-boilers (polymeric isocyanates, hydrolyzable chloride compounds, and other non-volatiles), the rest being toluenediisocyanate.

As used herein, unless otherwise expressly specified, a low-boiler product or fraction refers to a product or fraction having a boiling temperature below the solvent. A high-boiler product or fraction refers to a product or fraction having a boiling temperature above the TDI.

Product Fraction P4 is an isocyanate-enriched product stream lean in high-boilers and reaction residues. Product Fraction P4 preferably comprises of 20 to 100% by weight of TDI, more preferably 30 to 100% by weight of TDI. Product Fraction P4 is optionally fed to a final solvent removal step when necessary and then fed to a TDI purification step to attain the proper product specification.

The fractionation process according to the present invention may be successfully utilized to produce four main product streams from TDI reaction product comprising less than 2% by weight of phosgene resulting from the reaction of toluene diamine with phosgene in the presence of a solvent solution or from this reaction in the gas phase with a solvent used in the quench cooling after the reaction. The resulting distillation feed contains phosgene and other low-boiling components, solvent, toluene diisocyanate, hydrolyzable chloride compounds, and high-boiling residues. The four products are a phosgene-enriched low-boiler product P1, which is recovered and returned to the dephosgenation or excess phosgene recovery process, a relatively pure solvent product P2 which is then reused in the phosgenation or excess phosgene recovery process, a high-boiler enriched (polymeric isocyanate, hydrolyzable chloride compounds, and other non-volatiles) bottoms product P3 which is sent to a residue removal system for the further recovery of volatiles, and an isocyanate enriched stream P4. The solvent to be used can be any suitable solvent, preferably o-dichlorobenzene, p-dichloro-benzene, chlorobenzene, toluene, benzene, nitrobenzene, anisole, xylene, or any mixture thereof. Depending on reaction conditions different concentrations of TDI in the crude distillation feed can be obtained.

The process according to the present invention is performed in a heat integrated system comprising an upstream distillation column and a downstream distillation column which are connected in series and an interchanger which acts as the condenser for the upstream column and an vaporizer for the downstream column. This interchanger can be any of the standard types of vaporizers commonly found in the chemical industry, including in part falling-film vaporizers, forced circulation vaporizers, pool boiling (kettle) vaporizers, natural circulation vaporizers, etc, wherein the hot zone is separated from the cold zone by a heat transfer surface and the vapor product from the upstream column is condensed to provide the energy for the vaporization of the bottoms product from the downstream distillation column. The columns can be equipped with any mass transfer internals that are in common use in the chemical industry. These include, in part, sieve trays, valve trays, fixed valve trays, as well as structured or random distillation packings. The downstream distillation column is additionally equipped with a condenser. The condenser can be any of the types in common use in the chemical industry including co-current and countercurrent (knockback condensers).

In one embodiment of the current invention (FIGS. 1 and 2), the crude distillation feed is fed directly to the upstream distillation column. The interchanger acts as the condenser for the upstream distillation column and as a pre-vaporizer for the feed to the downstream distillation column. In this embodiment the crude distillation feed has a preferred concentration of from 5–30% by weight, more preferred of from 7–25% by weight, and most preferred of from 10–20% by weight TDI.

In a second embodiment of the current invention (FIGS. 3 and 4), the crude distillation feed is fed directly to the upstream distillation column. The interchanger acts as the condenser for the upstream distillation column and as the reboiler for the downstream distillation column. In this embodiment the crude distillation feed has a preferred concentration of from 5–30% by weight, more preferred of from 7–25% by weight, and most preferred of from 10–20% by weight TDI.

The invention is described in more detail in the following with reference to the accompanying drawings, wherein FIG. 1 shows a schematic of the heat integrated system comprising an upstream distillation column and a downstream distillation column which are connected in series which is used in the process for the purification of mixtures of TDI. In this scheme the interchanger acts as the condenser for the upstream distillation column and as a pre-vaporizer for the downstream distillation column. Additionally, here the solvent product P2 is taken as a sidedraw product with the top stages in the column used for the removal of low-boilers from the solvent.

Figure 2:
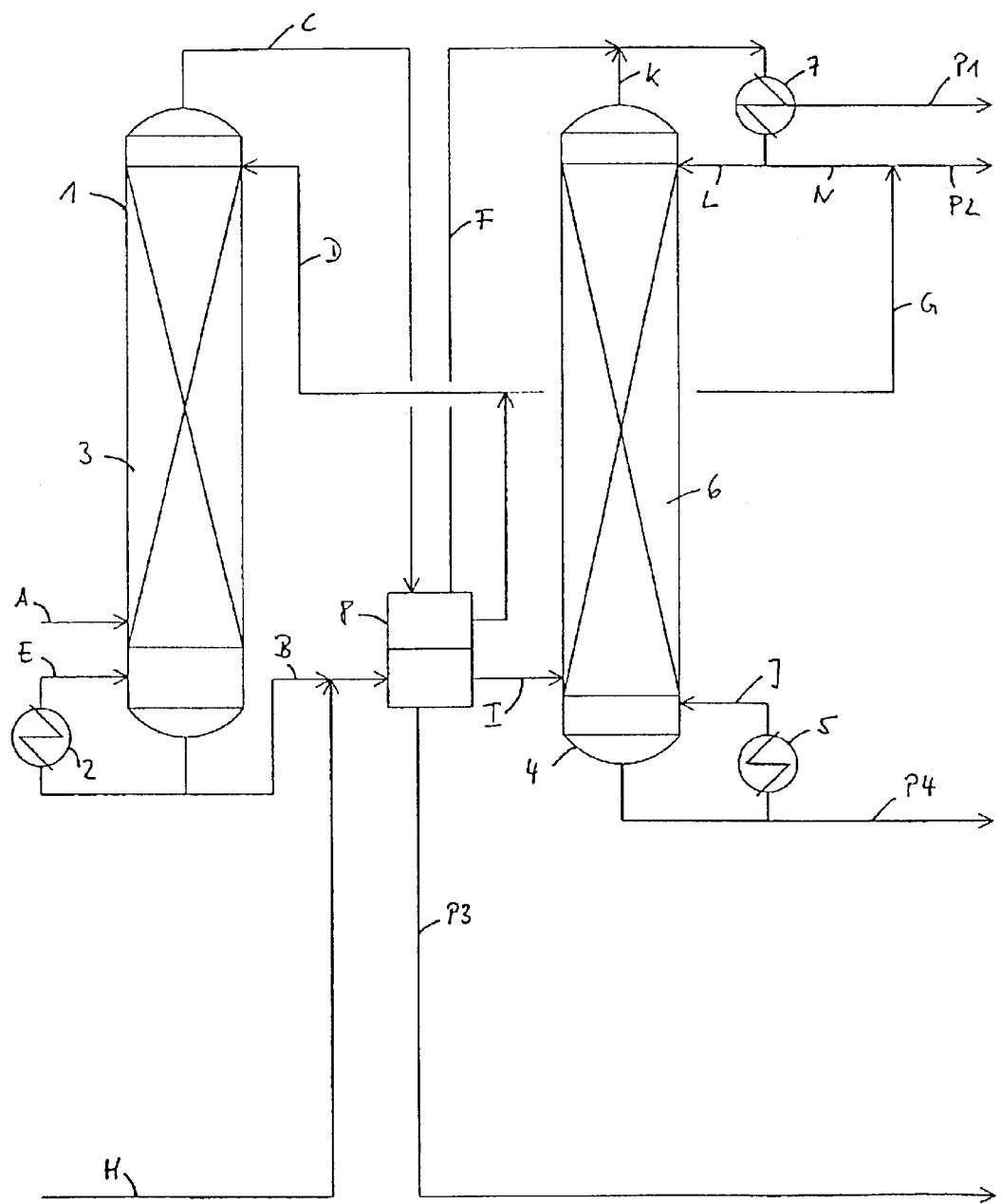
FIG. 2 is a schematic diagram of a second heat integrated system comprising an upstream distillation column and a downstream distillation column which are connected in series.

FIG. 2 shows a schematic of the heat integrated system comprising an upstream distillation column and a downstream distillation column which are connected in series which is used in the process for the purification of mixtures of TDI. In this scheme the interchanger acts as the condenser for the upstream distillation column and as a pre-vaporizer for the downstream distillation column. Here the solvent product P2 is removed as an overhead liquid product with no removal of low-boilers from the solvent. In this case, the solvent products from the upstream and downstream column are combined and sent to a stripping column for removal of low-boilers (not shown).

Figure 3:
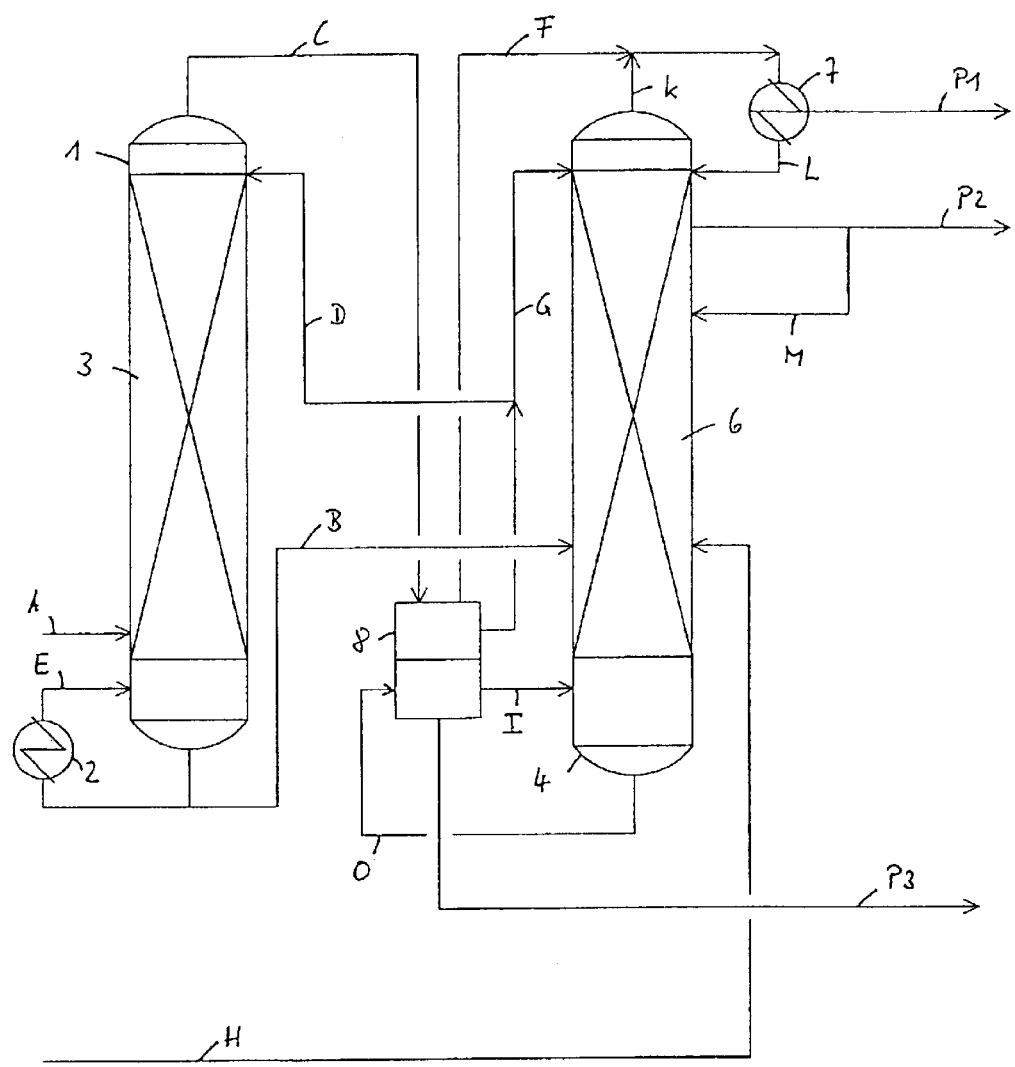
FIG. 3 is a schematic diagram of a third heat integrated system comprising an upstream distillation column and a downstream distillation column which are connected in series.

FIG. 3 shows a schematic of the heat integrated system comprising an upstream distillation column and a downstream distillation column which are connected in series which is used in the process for the purification of mixtures of TDI. In this scheme the interchanger acts as the condenser for the upstream distillation column and as the reboiler for the downstream distillation column. In the process shown in FIG. 3, the solvent product P2 is taken as a sidedraw product with the top stages in the column used for the removal of low-boilers from the solvent.

Figure 4:
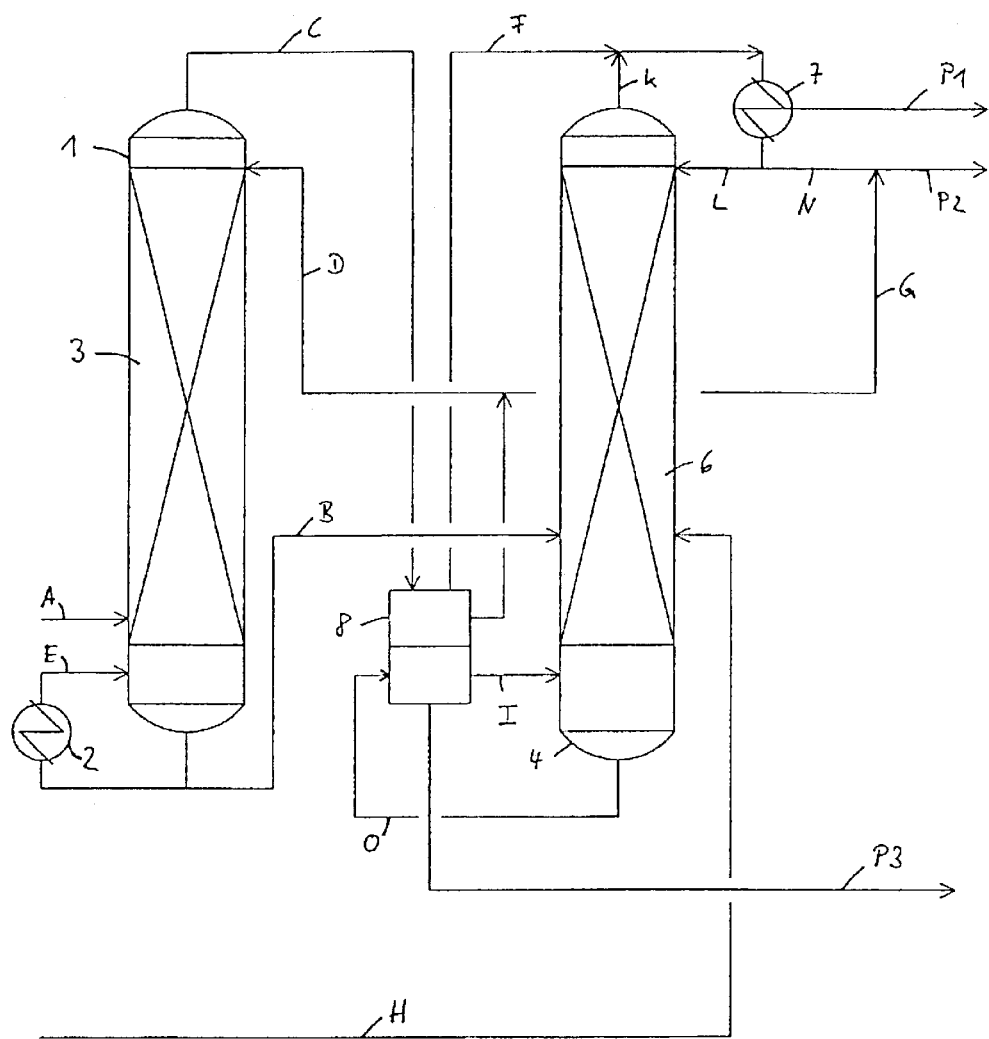
FIG. 4 is a schematic diagram of a fourth heat integrated system comprising an upstream distillation column and a downstream distillation column which are connected in series.

FIG. 4 shows a schematic of the heat integrated system comprising an upstream distillation column and a downstream distillation column which are connected in series which is used in the process for the purification of mixtures of TDI. In this scheme the interchanger acts as the condenser for the upstream distillation column and as the reboiler for the downstream distillation column. The solvent product P2 is removed as an overhead liquid product with no removal of low-boilers from the solvent. The solvent products from the upstream and downstream column are combined and sent to a stripping column for removal of low-boilers (not shown).

FIGS. 1 and 2 show heat integrated systems according to the present invention comprising:
an upstream distillation column 1 which is equipped with a reboiler 2, and mass transfer internals 3
a downstream distillation column 4 which is equipped with a reboiler 5 (optional), mass transfer internals 6, and a condenser 7 and an interchanger 8 which acts as a the condenser for the upstream distillation column 1 and as a pre-vaporizer for the feed to the downstream distillation column 4.

Upstream Distillation Column

The crude distillation feed A is fed to the upstream distillation column 1 (prefractionation), wherein it is separated into two streams, a low-boiler and isocyanate-enriched liquid stream B and a solvent and low-boiler enriched vapor stream C which are then fed to the interchanger 8. The reflux D is used together with a vapor product stream E from the reboiler 2 to effect the fractionation in the upstream distillation column 1.

Interchanger

The top vapor product C and the bottom liquid product B from the upstream distillation column 1 are fed to the condensing (hot) and vaporizing (cold) zones of the interchanger 8, respectively. In the interchanger 8, the vapor stream C is almost completely condensed and the subsequent energy from this condensation is used to evaporate a portion of the liquid stream B and stream H which comprises the recovered condensibles from the residue removal process. Any non-condensed vapor (stream F) is fed along with the top vapor product K from the downstream column 4 to the condenser 7 of the downstream distillation column 4. A portion of the condensed liquid is returned to the upstream distillation column 1 as reflux D. In FIG. 1, the solvent product P2 is a sidedraw. In this case, the remainder of the liquid condensate G is optionally cooled and subsequently fed to the top of the downstream distillation column 4 for the removal of phosgene and low-boilers. In an alternate embodiment (FIG. 2), the solvent product G from the interchanger 8 as well as the solvent product N from the downstream distillation column are mixed to obtain P2 and then fed to a separate stripping column (not shown). In the vaporizing zone of the interchanger 8, a mixture of the liquid stream B as well as a TDI and high-boiler enriched stream H from residue removal are partially vaporized resulting in the vapor stream I, which is fed to the downstream distillation column 4 and the liquid high-boiler and residue enriched bottoms product P3 which is sent to a residue removal system for the further recovery of volatiles.

Downstream Distillation Column

The vapor product I from the interchanger 8 is fed to the downstream distillation column 4 where the fractionation is completed to produce a low-boilers and phosgene enriched vapor stream P1 containing non-condensibles, a solvent product stream P2 and an isocyanate enriched bottoms product stream P4. The fractionation is effected by the condensation of the vapor streams F and K as from the interchanger 8 and downstream column 4, respectively, in condenser 7 with the reflux L returned to the downstream distillation column 4. In FIG. 1, the total mass of condensate L is returned to the downstream distillation column 4 and the solvent product P2 is removed as a sidedraw with a sidestream reflux M is returned to the downstream distillation column 4 to attain the proper product quality for product P2. This configuration allows the production of a solvent product P3 which is lean in phosgene and other low-boilers. Optionally, the downstream distillation column 4 can be designed with a stream N removed as an overhead liquid product (FIG. 2). In this configuration, condensate from condenser 7 is returned to the downstream distillation column 4 as reflux L in an amount which is sufficient to maintain the proper isocyanate concentration in the solvent product P2. The remainder N and the solvent product G from the upstream distillation column 1 are combined to form stream P2 and fed to a stripper (not shown) to reduce the phosgene and low-boiler concentration. As can be seen in FIGS. 1 and 2, the downstream distillation column 4 can be optionally equipped with a reboiler 5 to enable higher isocyanate concentrations in the product P4 to be reached. The vapor stream J helps to effect the fractionation, in this case. The product P4 is then fed from the downstream distillation column 4 to a final solvent removal step which is then followed by a TDI purification step or when possible directly to a TDI purification step.

FIGS. 3 and 4 show heat integrated systems according to the present invention comprising:

an upstream distillation column 1 which is equipped with a reboiler 2, and mass transfer internals 3 a downstream distillation column 4 which is equipped with mass transfer internals 6 and a condenser 7 an interchanger 8 which acts as a condenser for the upstream distillation column 1 and as a reboiler for the downstream distillation column 4.

Upstream Distillation Column

The crude distillation feed A is fed to the upstream distillation column 1, wherein it is separated into two streams, a low-boiler and isocyanate-enriched liquid stream B and a solvent and low-boiler enriched vapor stream C. Stream C is fed to the condensing (hot) zone of the interchanger 8. The reflux D is used together with a vapor product stream E from the reboiler 2 to effect the separation in the upstream distillation column.

Interchanger

The top vapor product C from the upstream distillation column 1 is fed to the condensing (hot) zone of the interchanger 8, while the bottoms product O from the downstream distillation column 4 is fed to the vaporizing (cold) zone of the interchanger 8. In the interchanger 8 the vapor stream C is almost completely condensed and the subsequent energy from this condensation is used to evaporate a portion of the liquid stream O. Any non-condensed vapor (stream F) is fed together with the vapor stream K from the downstream distillation column 4 to the condenser 7. A portion of the condensed liquid is returned to the upstream distillation column 1 as reflux D. In FIG. 3, the solvent product P2 is a sidedraw. In this case, the remainder of the liquid condensate G is optionally cooled and subsequently fed to the top of the downstream distillation column 4 for the removal of phosgene and low-boilers. In an alternate embodiment (FIG. 4), the solvent product G from the interchanger 8 as well as the solvent product N from the downstream distillation column 4 are combined to form P2 and fed to a separate stripping column (not shown). In the vaporizing (cold) zone of the interchanger 8, stream O which is the liquid product from the downstream distillation column 4 is partially vaporized resulting in the vapor stream I, which is fed to the downstream distillation column 4 and the liquid high-boiler and residue enriched bottoms product P3 which must undergo the removal of any remaining solvent as well as residue removal and TDI purification (not shown), when necessary.

Downstream Distillation Column

The vapor product I from the interchanger 8 is fed to the downstream distillation column 4 where the fractionation is completed to produce a low-boilers and phosgene enriched vapor stream P1 containing non-condensibles, and a solvent product stream P2. The fractionation is effected by the condensation of the vapor stream K in the condenser 7 with the reflux L returned to the downstream distillation column 4. In FIG. 3 the total mass of condensate K is returned to the downstream distillation column 4 and the solvent product P2 is removed as a sidedraw with a sidestream reflux M returned to the downstream distillation column 4 to attain the proper product quality for product P2. This configuration allows the production of a solvent product P3 which is lean in phosgene and other low-boilers. Optionally, the downstream distillation column 4 can be designed so that condensate is returned as reflux L to the downstream distillation column 4 in an amount which is sufficient to maintain the proper isocyanate concentration in the solvent product N. Stream N and the solvent product G from the upstream distillation column 1 are combined to form P2 and fed to a stripper (not shown) to reduce the phosgene and low-boiler concentration (FIG. 4).

EXAMPLES

Example 1

Example 1 has been performed in a system of heat integrated distillation columns for the partial removal of solvent from a TDI mixture wherein the heat of the vapor of the upstream distillation column is used to vaporize the feed to the downstream column in the manner shown in FIG. 1.

A crude reaction mixture, containing 1000 kg/h toluenediisocyanate is completely dephosgenated and the dephosgenated reaction product is mixed with solvent from process sources (i.e. washers, vacuum systems, etc.), and the volatiles recovered from the residue removal to yield a crude distillation feed A with a mass flowrate of 10534 kg/h at a temperature of 149° C., which is in the liquid phase at atmospheric pressure. The crude distillation feed A has the following composition by weight: 10.5% toluenediisocyanate (TDI), 0.2% TDI-residue, 0.006% hydrolyzable chloride compounds (HCC), and a trace amount of low-boilers and noncondensables, with the rest being o-dichlorobenzene. The bottoms products of the upstream distillation column 1 is partially vaporized to generate the vapor stream E and the liquid product B. Stream B has a flowrate of 6298 kg/h which is at a saturation point of 180° C. at 878 mbar. Stream B has a composition by weight of 17.5% TDI, 0.3% residue, 0.01% hydrolyzable chlorides, and the rest being ODB. Stream B is mixed with the bottoms product H from the TDI purification column (not shown) and fed to the vaporizing zone of the interchanger 8. Vapor stream E is fed to the upstream distillation column 1 which has 13 theoretical stages of structured packing 3 in the rectification zone. The upstream distillation column 1 operates at a top pressure of 864 mbar with a pressure drop of 14 mbar. Stream E as well as the reflux stream D effect the necessary fractionation in the upstream distillation column 1. The vapor product C from the upstream distillation column 1 is fed to the condensing zone of the interchanger 8.

In the interchanger 8, the vapor stream C from the upstream distillation column 1 is almost completely condensed and the energy is used to partially vaporize the mixture of streams B and H. All noncondensibles and uncondensed vapors (stream F) are fed to the condenser 7 of the downstream distillation column 4. Stream F is at 165° C. and 864 mbar and has a flowrate of 50 kg/h and a weight composition of 5% inert gases and 95% o-dichlorobenzene. A portion of the condensate is fed as reflux D to the upstream distillation column 1. The remainder of the condensate, stream G is fed to the top stage of the downstream distillation column 4 to effect the removal of phosgene and other low-boilers from the solvent product. G is a saturated liquid at 165° C. and 864 mbar. It has a flowrate of 4233 kg/h and a composition of 10 ppm by weight TDI with between 300 and 400 ppm lowboilers and the rest being o-dichlorobenzene. In this case a reflux ratio of 0.334 is maintained for the upstream distillation column 1 to achieve a TDI concentration in stream G of 10 ppm by weight TDI. The resulting vapor product I from the vaporizing zone of the interchanger 8 is fed to the downstream distillation column 4, the remaining product P3 is fed to the residue removal system (not shown). The product P3 is a saturated liquid at 157° C. and 224 mbar. It has a flowrate of 178 kg/h and a weight composition 30.6% o-dichlorobenzene, 10% residue, 0.13% hydrolyzable chlorides, and the rest TDI.

The downstream distillation column 4 is designed with 19 theoretical stages of structured packing. The column operates at a top pressure drop of 205 mbar and a pressure drop over the column of 20 mbar. The vapor stream I from the interchanger, 8 is fed to the downstream distillation column 4 below the packing. In this column, fractionation is performed to achieve a bottoms product P4 that is enriched in TDI, a vapor product P1 enriched in non-condensibles and low-boilers and a solvent product P2, lean in TDI and low-boiler species. This fractionation is effected by the condenser 7 and the reboiler 5. In the condenser 7, the vapor product K from the downstream distillation column 4 as well as the uncondensed vapor from the condensing zone of the interchanger (stream F) are almost completely condensed, resulting in the vapor stream P1, and the condensate stream L. Stream P1 has a flowrate of 50 kg/h and a composition by weight 20% non-condensibles and 80% o-dichlorobenzene at a temperature of 102° C. and a pressure at 205 mbar. Stream L as well as stream G are fed to the top of the downstream distillation column 4. In this example, the downstream distillation column 4 is designed to provide 1 theoretical stripping stage for the separation of low-boilers from the o-dichlorobenzene product P2. The o-dichlorobenzene product, P2 is removed as a sidedraw product. P2 is a saturated liquid at 125° C. and 207 mbar, and has a flowrate of 8811 kg/h. It has a composition by weight of 10 ppm TDI with the rest being o-dichlorobenzene. A reflux ratio of 0.266 is required for the downstream distillation column 4 to reach this product purity. The product P4 is taken from the sump of the downstream distillation column 4 and is fed to an additional distillation column (not shown) for the removal of the remaining solvent and the subsequent purification of the TDI product. Product P4 is a saturated liquid at 155° C. and 224 mbar. It has a flowrate of 1676 kg/h and a composition by weight of 32.4% o-dichlorobenzene, 0.09% hydrolyzable chlorine, and the rest being TDI.

The process according to Example 1 uses a heat integrated system comprising an upstream distillation column 1 and a downstream distillation column 4 which are connected in series according to the invention. The total TDI fractionation process, inclusive solvent removal, TDI purification, and residue removal, requires a specific energy usage of 0.83 kWh/kg The process according to Chem. System's *PERP Report for TDI/MDI* (Chem. Systems, Process Evaluation Research Planning TDI/MDI 98/99S8. Tarrytown, N.Y., USA: Chem. Systems, 1999, pp 27–32) uses an initial solvent removal step instead of the heat integrated system. This results in a higher specific energy consumption. Accordingly, the usage of the process according to the present invention (Example 1) results in energy savings of 26.8% compared with the usage of the process disclosed in Chem. System's *PERP Report for TDI/MDI* (Comparison of total TDI fractionation process inclusive solvent removal, TDI purification, and residue removal).

The usage of the process according to the present invention (Example 1) also results in energy savings of 26.5% and 27.6% compared with the usage of the process disclosed in Oertel, G. (Editor), Polyurethane Handbook, Munich, Germany: Hanser Publishers, 1985, pp 62–73 and the process disclosed in Franck H.-G. and Stadelhofer J., Industrielle Aromatenchemie. Berlin, Germany: Springer Verlag, 1987, p. 253, respectively (Comparison of total TDI fractionation process inclusive solvent removal, TDI purification, and residue removal).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for the purification of toluenediisocyanate by fractionating a crude distillation feed comprising toluenediisocyanate, an organic solvent and less than 2% by weight of phosgene in a heat integrated system comprising an upstream distillation column, an interchanger and a downstream distillation column which are connected in series, wherein the vapor which is recovered from the upstream distillation column is used to reboil the bottoms product of the downstream distillation column or the feed to the downstream distillation column in the interchanger, and wherein the crude distillation feed comprising less than 2% by weight of phosgene is fractionated into three product fractions P1–P3 and optionally a fourth fraction P4, wherein P1 is a noncondensible gas stream enriched with phosgene and/or low-boilers, P2 is a solvent-enriched product, P3 is a high boiler enriched bottoms product comprising toluenediisocyanate and P4 is a toluenediisocyanate enriched stream lean in highboilers and reaction residues.

2. The process of claim 1 wherein the noncondensible gas stream enriched with phosgene and/or low boilers product fraction P1 comprises 20–50% by weight of phosgene and other low-boilers, 20–49% by weight of solvent, and non-condensible gases.

3. The process of claim 1, wherein the solvent-enriched product fraction P2 comprises of solvent with an isocyanate concentration of less than 100 ppm by weight and a phosgene concentration of less than 100 ppm by weight.

4. The process of claim 1, wherein the fraction P3 high boiler enriched bottoms product comprises toluenediisocyanate and 0.5–15% by weight of high-boilers.

5. The process of claim 1, wherein the toluene diisocyanate enriched stream lean in high boilers and reaction residues product fraction P4 comprises from 20 to 100% by weight of toluenediisocyanate.

6. The process of claim 1, wherein the solvent is at least one of o-dichloro-benzene, p-dichlorobenzene, chlorobenzene, toluene, benzene, nitrobenzene, anisole, and xylene.

* * * * *